United States Patent
Tabuchi et al.

(10) Patent No.: US 7,368,123 B1
(45) Date of Patent: May 6, 2008

(54) PESTICIDAL RESIN COMPOSITIONS AND PESTICIDAL PRODUCTS FORMED FROM THE SAME

(75) Inventors: Akira Tabuchi, Tokushima (JP);
Kiyozumi Tani, Tokushima (JP);
Akiyoshi Inubushi, Tokushima (JP);
Atushi Kamada, Tokushima (JP);
Masaharu Kamei, Tokushima (JP);
Osamu Igarashi, Yokohama (JP)

(73) Assignees: Otsuka Kagaku Kabushiki Kaisha (JP); NIX, Inc. (JP)

( * ) Notice: Subject to any disclaimer, the term of this patent is extended or adjusted under 35 U.S.C. 154(b) by 0 days.

(21) Appl. No.: 09/889,130

(22) PCT Filed: Jan. 14, 2000

(86) PCT No.: PCT/JP00/00160

§ 371 (c)(1),
(2), (4) Date: Oct. 9, 2001

(87) PCT Pub. No.: WO00/41564

PCT Pub. Date: Jul. 20, 2000

(30) Foreign Application Priority Data

Jan. 18, 1999 (JP) ................................ 11-009743

(51) Int. Cl.
*A01N 25/10* (2006.01)
(52) U.S. Cl. ...................... 424/409; 424/405; 424/406; 424/408; 424/421; 514/519; 514/521; 514/533
(58) Field of Classification Search ................ 424/405, 424/406–409, 411–413, 420, 421, 417, 419; 514/546–552, 561–565, 478–481, 506, 519–533, 514/601–605, 703, 708, 709; 560/17, 18
See application file for complete search history.

(56) References Cited

U.S. PATENT DOCUMENTS

| 4,184,099 | A |   | 1/1980  | Lindauer et al.         |
|-----------|---|---|---------|-------------------------|
| 4,405,360 | A | * | 9/1983  | Cardarelli ...... 71/117 |
| 5,374,600 | A | * | 12/1994 | Hozumi et al. ...... 502/402 |
| 5,614,568 | A | * | 3/1997  | Mawatari et al. ...... 523/122 |
| 5,948,836 | A | * | 9/1999  | Bonora ...... 524/99 |
| 5,965,150 | A | * | 10/1999 | Wada et al. ...... 424/408 |
| 6,063,393 | A | * | 5/2000  | Tsuboi et al. ...... 424/409 |

FOREIGN PATENT DOCUMENTS

| EP | 0569791   | 11/1993 |
| EP | 0 750 842 A | 1/1997 |
| JP | 3153601   | 7/1991  |
| JP | 69319     | 1/1994  |
| JP | 7157630   | 6/1995  |
| JP | 9169916   | 6/1997  |
| JP | 9221592   | 8/1997  |

* cited by examiner

*Primary Examiner*—Neil S. Levy
(74) *Attorney, Agent, or Firm*—Wood, Phillips, Katz, Clark & Mortimer

(57) ABSTRACT

According to the present invention, there is provided a pesticidal resin composition that contains (A) at least one resin selected from polyamide resins and polyacetal resins, (B) at least one compound selected from sulfone amide derivatives, sulfonic acid ester derivatives, phosphoric acid ester derivatives, phosphazene derivatives, carboxylic acid amide derivatives, carboxylic acid ester derivatives, and (C) a chemical agent having a pesticidal property. With the pesticidal resin composition containing the above ingredients, it is possible to obtain a pesticidal product that has such a strength, heat resistance and chemical resistance as to render the product usable as a structural member, as well as being capable of exhibiting the pesticidal activity for a prolonged period of time.

2 Claims, No Drawings

PESTICIDAL RESIN COMPOSITIONS AND PESTICIDAL PRODUCTS FORMED FROM THE SAME

TECHNICAL FIELD

The present invention relates to pesticidal resin compositions and pesticidal products formed from the same.

BACKGROUND ART

There exists a problem in that intrusion of insects or the like into electric equipment or transport equipment causes malfunctions or disorders thereof. For example, a TV receiver causes heat inside thereof, which may attract pests such as insects or spiders, which intrude into the inside of the TV receiver through small holes on a rear side thereof, and cause malfunction through short-circuit of a circuit, or the like. Such intrusion of insects or the like causing disorders sometimes occur in computers, telephone switchboards, industrial robots or the like.

To address the above problem, it is conceivable to prepare a pesticidal substance carried on a resin material used for structural member, exterior member, fluid transferring pipe, drive member or the like of the instruments.

As a resin material having a pesticidal property, there have been proposed a soft resin such as a low molecular weight straight-chain polyethylene resin, polypropylene resin or polyvinyl chloride resin that is blended as a matrix resin with an insecticide or the like. These resins are of the type that is capable of holding a large volume of a chemical agent such as an insecticide, but has a drawbacks, namely a poor strength, poor heat resistance and poor chemical resistance. Therefore, a product which is formed by using such a resin composition itself as a forming material is greatly limited in its application, and therefore is only applicable to such as a cat collar for which little strength is required (see Japanese Patent Application Laid-open Numbers Hei-6-315332, 5-284871, and 6-141724).

A so-called engineering plastic has an excellent heat resistance and chemical resistance. However, it usually exhibits a poor capability in carrying the chemical agent mentioned above. As a result, such a plastic mixed with the chemical agent exhibits no sustained release, produces no pesticidal effect or loses the pesticidal effect in a short period of time even if the initial effect can be produced, or poses any other drawbacks.

SUMMARY OF THE INVENTION

In consideration of the problems with the prior arts, it is an object of the present invention to provide a resin composition that has such a heat resistance and chemical resistance as to enable the resin composition to be used as a structural member or the like, as well as being capable of exhibiting the pesticidal activity for a prolonged period of time.

Specifically, according to the present invention, there is provided a pesticidal resin composition that contains (A) at least one resin selected from polyamide resins and polyacetal resins (hereinafter referred simply to "A component" in some cases), (B) at least one compound selected from sulfone amide derivatives, sulfonic acid ester derivatives, phosphoric acid ester derivatives, phosphazene derivatives, carboxylic acid amide derivatives, carboxylic acid ester derivatives (hereinafter referred simply to "B component" in some cases), and (C) a chemical agent having a pesticidal property (hereinafter referred simply to "C component" in some cases).

With the pesticidal resin composition containing the above ingredients, it is possible to obtain a pesticidal product that has such a strength, heat resistance and chemical resistance as to render the product usable as a structural member, as well as being capable of exhibiting the pesticidal activity for a prolonged period of time.

According to the present invention, the pesticidal resin composition may be mixed with (D) a fibrous inorganic filler (hereinafter referred simply to "D component"). The composition mixed with the fibrous inorganic filler can preferably achieve more improved sustained release. Also, the mixture of the fibrous inorganic filler is preferable since it contributes to improvement of mechanical property.

According to the present invention, there is also provided a pesticidal product formed from any one of the pesticidal resin compositions mentioned above. The pesticidal product may be manufactured by forming the pesticidal resin composition directly into a desirable shape, or by extruding the same and forming it temporarily into pellets or the like for storing and distributing. The forming to the pellets enables the shaping of the product by a known method.

BEST MODE FOR CARRYING OUT THE INVENTION

As specific examples of the polyamide resins in (A) at least one resin selected from polyamide resins and polyacetal resins, it can be cited polyamide resins such as polyamide-6, polyamide-66, polyamide-11, or polyamide-12 resin, and aromatic polyamide resins such as polyamide-MXD or polyamide-6T resin.

As specific examples of the polyacetal resins, it can be cited a homopolymer comprising oxymethylene unit only, as well as a copolymer comprising oxymethylene unit as a main component and a different copolymer unit such as oxyethylene unit as an accessory component, cross-linked polymer formed by the cross-linkage therebetween or graft copolymer formed by graft copolymerization therebetween.

It is possible to use, as the A component, solely the one selected from the polyamide resins or the one selected from the polyacetal resins, or the mixture comprising two or more resins selected from these resins.

The polyamide resins or polyacetal resins used as the A component in the present invention may be used in the form of alloy with different resins as far as it does not deteriorate the effects produced by the present invention. As specific examples of resins which can be employed as the different resins in this alloy, it can be cited polyethylene, polypropylene, polystyrene, acrylonitrile-butadiene-styrene resin, polyethylene terephthalate, polybutylene terephthalate, polycarbonate, polyarylate, polyphenylene ether, thermoplastic polyurethane, liquid crystal polyester and the like. These may be used as being mixed into the (A) component in an amount of less than 70 weight parts.

It is conceivable that at least one compound selected from (B) sulfone amide derivatives, sulfonic acid ester derivatives, carboxylic acid amide derivatives, carboxylic acid ester derivatives can dissolve and hold the (C) component, thus achieving an action enabling the composition to have sustained release.

As specific examples of the carboxylic acid ester derivatives among those used as the (B) component, it can be cited an alkyl ester, aromatic ester or the like of various carboxylic acids, for which a hydroxyl group, nitro group, amino group, epoxy group, halogen or the like may be substituted. Particularly, those with the hydroxyl group, epoxy group or the like are preferable for their favorable compatibility with polyamide.

As specific examples of the carboxylic acid ester derivatives, it can be cited phthalic acid ester derivatives such as dimethyl phthalate, diethyl phthalate, di-n-octyl-phthalate, diphenyl phthalate, benzyl phthalate, dimethoxy-ethyl-phthalate, 4,5-epoxy-hexahydro-phthalic-acid-di(2-ethyl hexyl), 4,5-epoxy-cyclohexahydro phthalic-acid (7,8-epoxy-2-octenyl), 4,5-epoxy-cyclohexahydro-phthalic-acid-di (9,10-epoxyoctadecyl), 4,5-epoxy-cyclohexahydro-phthalic-acid-di(10,11-epoxyundecyl), phthalic-acid-di (tetrahydrofurfuryloxyethyl), various phthalic acid mixed esters and an ethylene oxide adduct of a phthalic acid mixed ester, isophthalic acid ester derivatives, tetrahydrophthalic acid ester derivatives, benzoic acid ester derivatives such as parahydroxy benzoic acid butoxyethyl, parahydroxy benzoic acid cyclohexyloxy ethoxy ethoxyethyl, parahydroxy benzoic acid 2-ethylhexyl, hydroxybenzoic acid ester of ω-alkyl (oligo) ethylene oxide and a parahydroxy benzoic acid adduct of an undecyl glycidyl ether, propionic acid ester derivatives such as thiodipropionic acid di(tetrahydrofurfuryloxy ethyl), adipic acid ester derivatives, azelaic acid ester derivatives, sebacic acid ester derivatives, dodecane-2-acid ester derivatives, maleic acid ester derivatives, fumaric acid ester derivatives, trioctyl trimellitate ester derivatives, citric acid ester derivatives such as tri(buthoxy ethoxyethyl)citrate, di-n-octyl-mono(nonyl phenoxy ethyl)citrate, tri-n-octyl citrate, dioctyl(tetrahydrofurfuryloxy ethyl)citrate, trimyristyl citrate and triethyl citrate, itaconic acid ester derivatives, oleic acid ester derivatives such as tetrahydrofurfuryl oleate, ricinoleic acid ester derivatives, lactic acid ester derivatives such as (n-butyl)lactate, (2-ethylhexyl) lactate, (n-buthoxyethoxyethyl)lactate, (ethoxy-n-octoxy-ethyl)lactate and (n-decyloxyethoxyethyl)lactate, tartaric acid ester derivatives such as di(ethoxyoctoxyethyl)tartrate and (n-octyl) (nonylphenoxyethyl)tartrate, malic acid ester derivatives such as dibutoxyethyl malate, di(n-butoxyethoxyethyl)malate, distearyl malate and octadecinyl isononyl malate, salicylic acid ester derivatives such as a salicylic acid adduct of an benzyl glycidyl ether.

As specific examples of the phosphoric acid ester derivatives, it can be cited trimethyl phosphate, triethyl phosphate, tributyl phosphate, tris(2-ethylhexyl)phosphate, 2-ethylhexyldiphenyl phosphate, tributoxyethyl phosphate, triphenyl phosphate, crezyldiphenyl phosphate, isodecyldiphenyl phosphate, tricresyl phosphate, trixylenyl phosphate, tri (chloroethyl)phosphate, dimethylphenyl diphenyl phosphate, and tetrakis(2,4di-tertiary-butylphenyl)4,4'-biphenylen diphosphonate.

It can be cited, as specific examples of the phosphazene derivatives, cyclic phosphazene compounds having the general formula (1)

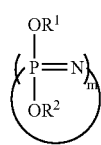

(1)

in which
m stands for an integer of 3 to 25, $R^1$, $R^2$ are equal or different and represent a $C_{1-8}$-alkyl group and a phenyl group which may be substituted with a $C_{1-8}$-alkyl group and/or aryl group, as well as straight chain phosphazene compounds having the general formula (2)

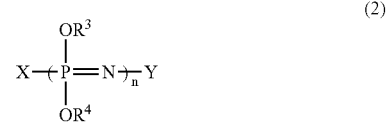

(2)

in which
n stands for an integer of 3 to 1000,
$R^3$, $R^4$ are equal or different and represent a $C_{1-8}$ alkyl group and a phenyl group which may be substituted with a $C_{1-8}$ alkyl group and/or aryl group,
X represents a group: —N=P(OR$^3$)$_3$, group: —N=P (OR$^4$)$_3$, group: —N=P(O)(OR$^3$) or group: —N=P(O) (OR$^4$),
Y represents a group: —P(OR$^3$)$_4$, group: —P(OR$^4$)$_4$, group: —P(O)(OR$^3$)$_2$ or group: —P(O)(OR$^4$)$_2$, as well as at least one phosphazene compound selected from the aforesaid phosphazene compounds in which
two oxygen atoms resulting from the releasing of alkyl groups or the like from substituents $R^1$, $R^2$, $R^3$, $R^4$ are linked to each other via at least one crosslinking group selected from the group consisting of o-, m-, p-phenylene group, biphenylene group and groups having the general formula (3)

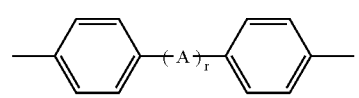

(3)

in which
r represents 0 or 1,
A represents a group: —SO$_2$—, —S—, —O—, or —C(CH$_3$)$_2$—.

As specific examples of the cyclic phosphazene compounds having the general formula (1), it can be cited hexa-phenoxy-cyclo-triphosphazene, octa-phenoxy-cyclo-tetraphosphazene, deca-phenoxy-cyclo-pentaphosphazene, hexa-propoxy-cyclo-triphosphazene, octa-propoxy-cyclo-tetraphosphazene, and deca-propoxy-cyclo-pentaphosphazene.

As specific examples of the straight chain phosphazene compounds having the general formula (2), it can be cited chain phosphazene compounds each having a chain dichlorphosphazene with which a propoxy group and/or phenoxy group are substituted.

As specific examples of the crosslinking structure having the general formula (3), it can be cited 4,4'-sulfonyldiphenylene(bisphenol-S-residue), 4,4'-oxydiphenylene group, 4,4'-thiodiphenylene group, and 4,4'-diphenylene group.

These phosphazene derivatives each may have a portion or portions which are substituted with an amino group and/or phenylamino group.

Those phosphazene derivatives each may be solely used, or the mixture of two or more derivatives may be used. Also, the mixture of a cyclic phosphazene and a straight chain phosphazene may be used.

As a specific example of the carboxylic acid amide derivatives, it can be cited N-cyclohexyl benzoic acid amide or the like.

As specific examples of the sulfone amide derivatives, it can be cited N-methyl-benzenesulfonamide, N-ethyl-benzenesulfonamide, N-butyl-benzenesulfonamide, N-cyclohexyl-benzenesulfonamide, N-ethyl-P-toluenesulfonamide, N-butyl-toluenesulfonamide, and N-cyclohexyl-toluenesulfonamide.

As a specific example of the sulfonic acid ester derivatives, it can be cited benzene sulfonic acid ethyl or the like.

As the (B) component, one derivative selected from sulfone amide derivatives, sulfonic acid ester derivatives, carboxylic acid amide derivatives and carboxylic acid ester derivatives may be solely used, or a mixture of two or more derivatives selected therefrom may be used.

The (C) chemical agent having a pesticidal property is a chemical agent exhibiting pesticidal activity against various agricultural harmful insects, insanitary insects or pests such as any other insects, spiders, mites or rats. It can be cited as the (C) chemical agent compounds exhibiting a pest repellent activity, compounds exhibiting insecticidal, miticidal, spidercidal, rodenticidal or any other pesticidal activity, compositions exhibiting antifeedant activity, pest growth control activity, and the like.

As specific examples of the chemical agent having such a pesticidal property, it can be cited chloronicotinyl insecticides such as imidacloprid insecticide, compounds having silicon atoms such as silafluofen, carbamate compounds such as benfuracarb, alanicarb, metoxadiazone [5-methoxy-3-(2-methoxyphenyl)-1,3,4-oxadiazole-2(3H)-one], carbosulfan, phenobcarb, carbaryl, methomyl, propoxur and phenoxycarb, pyrethroid compounds such as pyrethrin, allethrin, d1,d-T80-allethrin, d-T80-resmethrin, bioallethrin, d-T80-phthalthrin, phthalthrin, resmethrin, furamethrin, proparthrin, permethrin, acrinathrin, etofenprox, tralomethrin, phenothrin, d-phenothrin, fenvalerate, empenthrin and prarethrin, tefluthrin, organophosphorous compounds such as dichlorovos, fenitrothion, diazinon, malathion, propaphos, fenthion, trichlorform, naled, temephos, fenclophos, chlorpyriphosmethyl, ciafos, calcrofos, azamethiphos, pyridafenthion, propetamphos and chlorpyriphos, as well as their isomers, derivatives and affinities.

As specific examples of the compounds exhibiting pest growth control activity, it can be cited methoprene, pyriproxyfen, kinoprene, hydroprene, diofenolan, NC-170, flufenoxuron, diflubenzuron, lufenuron and chlorfluazuron.

As specific examples of miticides, it can be cited kelthane, chlorfenapyr, tebufenpyrad, pyridaben, milbemectin, and fenpyroximate. As specific examples of rodenticides, it can be cited scilliroside, norbormide, zinc phosphide, thallium sulfate, yellow phosphor, antu, warfarin, coumarine, coumatetralyl, bromadiolone and difethialone.

As the (D) fibrous inorganic filler, those having an average fiber diameter of 0.05 to 10 m, an average fiber length of 3 to 150 μm are preferably used, and it can be cited as specific examples thereof potassium 4-titanate fiber, potassium 6-titanate fiber, potassium 8-titanate fiber, titania fiber, monoclinic titania fiber, silica fiber, wollastonite and zonotlite. These may be each solely used or used as mixed with each other. Among these fibrous inorganic fillers, the potassium 8-titanate fiber is most preferable.

The fibrous inorganic filler is preferably mixed into a compound because it achieves more improved sustained release. Also, the mixture of the fibrous inorganic filler is preferable since it contributes to improvement of mechanical property.

While the fibrous inorganic filler may be used as it is, it may be subjected to surface treatment with a surface treating agent such as a silane coupling agent such as amino silane, epoxy silane and acrylic silane, or a titanate coupling agent.

An inorganic filler such as zeolite may be used together in a resin composition of the present invention to such an extent as not to deteriorate the object of the present invention.

While the mixing proportion of each component in the resin composition of the present invention may be suitably set according to an actually selected component, a usual proportion is such that the (B) component is set within the range of 0.05 and 100 weight parts and preferably 2 and 50 weight parts, and the (C) component is set within the range of 0.01 and 30 weight parts and preferably 0.1 to 20 weight parts with respect to 100 weight parts of the (A) component Where the (D) component is mixed, its mixing proportion is preferably 2 to 60 weight part with respect to 100 weight parts of the (A) component. When the mixing proportion of the (D) component is more than 60 weight parts, it poses a difficulty in shaping. On the contrary, when the mixing proportion is less than 2 weight parts, a mixing effect of the fibrous inorganic filler may not sufficiently produced.

The pesticidal resin composition of the present invention may be manufactured for example by mixing the respective components together, and then melting and kneading the same. The respective components may be mixed together by dry-blending technique using a tumbler, blender, mixer, etc. Alternatively, the mixing of these components may be made by the feeding of the components through the same hopper or different hoppers of a kneading machine.

The pesticidal resin composition obtained may be directly formed into a desirable shape for use as a pesticidal product, or may be extruded and formed temporarily into pellets or the like for storing and distributing. The reason for forming the composition to the pellets or the like is that they may be processed into a shape by a known method.

For shaping the pesticidal resin composition of the present invention, various known shaping techniques may be employed. For example, injection molding, extrusion molding, press molding, blow molding, or machining technique may be used.

The pesticidal product of the present invention is not necessarily limited to a specific shape. Rather, it may be formed in flat plate, stick, cylinder, comb, sphere, or any shape.

The pesticidal resin composition may be combined with conventional resin compositions, metals or the like, and formed into such as a structural member in two or more than two colors, a desirable part of which structural member exhibiting the pesticidal activity.

EMBODIMENTS

The present invention will be discussed in more detail by illustrating embodiments and comparative examples as below.

Embodiments 1 to 3 and Comparative Examples 1 to 4

By using a biaxial extruder of 45 mm φ with a resin temperature set at 190° C., the (A) component (for which polyamide 12, represented by "PA" in the type-indicating fields of the TABLES herein, was used as a polyamide resin) was poured thereinto and molten. The polyamide 12 used is marketed under the name "DAIAMID L-1940" and manufactured by DAICEL-HÜLS LTD. The mixture of the (B) component (for which N-butyl-benzenesulfonamide, represented by "A" in the type-indicating fields of the TABLES herein, was used as a sulfone amide derivative) and the (C) component (for which permethrin, represented by "A" in the type-indicating fields of the TABLES herein, was used as a pesticide) in the proportions stated in the TABLE 1 or 2 was placed into the biaxial extruder through a side hopper thereof with pressure by a plunger pump and formed into pellets. Thus, the resin compositions of the embodiments 1 to 3, and the comparative examples 1 to 4 were obtained.

The molded articles for the testing each having a cylindrical shape with an inner diameter of 15 mm ϕ, thickness of 1.5 mm and length of 40 mm were prepared by an injection molding machine, using the pellets obtained.

However, the resin composition of the comparative example 4 had a chemical agent bled-out on the surfaces of the pellets, so that an injection molded article could not be prepared.

under the name "DURACON M90-44" and manufactured by POLYPLASTICS CO., LTD. The mixture of the (B) component (for which N-butyl-benzenesulfonamide was used as a sulfone amide derivative) and the (C) component (for which permethrin was used as a pesticide) in the proportions stated in the TABLES 1 or 2, was placed into the biaxial extruder through a side hopper thereof with pressure by a plunger pump and formed into pellets. Thus, the resin compositions of the embodiments 4 to 6, and the comparative example 5 were obtained.

The molded articles for the testing each having a cylindrical shape with an inner diameter of 15 mm ϕ, thickness of 1.5 mm and length of 40 mm were prepared by an injection molding machine, using the pellets obtained.

Embodiments 7 to 9

The resin compositions of embodiments 7 to 9 were obtained in the same manner as the first embodiment except

TABLE 1

| Embodiments | (A) component | | (B) component | | (C) component | | (D) component | | Pesticidal activity | | |
|---|---|---|---|---|---|---|---|---|---|---|---|
| | Types | Mixed amts. | Types | Mixed amts. | Types | Mixed amts. | Types | Mixed amts. | 7 days | 3 months | 6 months |
| 1 | PA | 80 | A | 15 | A | 5 | — | — | ○ | Δ | X |
| 2 | PA | 75 | A | 15 | A | 10 | — | — | ○ | ○ | X |
| 3 | PA | 65 | A | 15 | A | 20 | — | — | ○ | ○ | X |
| 4 | POM | 85 | A | 10 | A | 5 | — | — | ○ | Δ | X |
| 5 | POM | 80 | A | 10 | A | 10 | — | — | ○ | Δ | X |
| 6 | POM | 70 | A | 10 | A | 20 | — | — | ○ | ○ | Δ |
| 7 | PA | 80 | A | 15 | B | 5 | — | — | ○ | Δ | X |
| 8 | PA | 75 | A | 15 | B | 10 | — | — | ○ | Δ | X |
| 9 | PA | 65 | A | 15 | B | 20 | — | — | ○ | Δ | Δ |
| 10 | PA | 80 | B | 15 | A | 5 | — | — | ○ | Δ | X |
| 11 | PA | 75 | B | 15 | A | 10 | — | — | ○ | Δ | X |
| 12 | PA | 65 | B | 15 | A | 20 | — | — | ○ | Δ | Δ |
| 13 | PA | 80 | C | 15 | A | 5 | — | — | ○ | Δ | X |
| 14 | PA | 75 | C | 15 | A | 10 | — | — | ○ | Δ | Δ |
| 15 | PA | 65 | C | 15 | A | 20 | — | — | ○ | ○ | Δ |
| 16 | PA | 70 | A | 15 | A | 5 | A | 10 | ○ | ○ | Δ |
| 17 | PA | 60 | A | 15 | A | 5 | A | 20 | ○ | ○ | Δ |
| 18 | PA | 65 | A | 15 | A | 10 | A | 10 | ○ | ○ | ○ |
| 19 | PA | 55 | A | 15 | A | 10 | A | 20 | ○ | ○ | ○ |
| 20 | PA | 55 | A | 15 | A | 20 | A | 10 | ○ | ○ | ○ |
| 21 | PA | 45 | A | 15 | A | 20 | A | 20 | ○ | ○ | ○ |

TABLE 2

| Comparative examples | (A) component | | (B) component | | (C) component | | (D) component | | Pesticidal activity | | |
|---|---|---|---|---|---|---|---|---|---|---|---|
| | Types | Mixed amts. | Types | Mixed amts. | Types | Mixed amts. | Types | Mixed amts. | 7 days | 3 months | 6 months |
| 1 | PA | 85 | A | 15 | — | 0 | — | — | X | — | — |
| 2 | PA | 95 | — | 0 | A | 5 | — | — | ○ | X | — |
| 3 | PA | 90 | — | 0 | A | 10 | — | — | ○ | X | — |
| 4 | PA | 80 | — | 0 | A | 20 | — | — | — | — | — |
| 5 | POM | 90 | A | 10 | — | 0 | — | — | X | — | — |
| 6 | PP | 80 | — | 0 | A | 20 | — | — | — | — | — |
| 7 | EVA | 80 | — | 0 | A | 20 | — | — | — | — | — |

Embodiments 4 to 6 and Comparative Example 5

By using a biaxial extruder of 45 mm ϕ with a resin temperature set at 185° C., the (A) component (for which polyacetal resin, represented by "POM" in the type-indicating fields of the TABLES herein, was used) was poured thereinto and molten. The polyacetal resin used is marketed for the (C) component, for which methoxydiazone (a pesticide represented by "B" in the type-indicating fields of the TABLES herein) was alternatively used.

Also, the molded articles for the testing each having a cylindrical shape with an inner diameter of 15 mm ϕ, thickness of 1.5 mm and length of 40 mm were prepared by an injection molding machine, using the pellets obtained.

Embodiments 10 to 12

The resin compositions of embodiments 10 to 12 were obtained in the same manner as the first embodiment except for the (B) component, for which parahydroxybenzoic acid 2 ethylhexl (a carboxylic acid ester derivative, represented by "B" in the type-indicating fields of the TABLES herein) was alternatively used.

Also, the molded articles for the testing each having a cylindrical shape with an inner diameter of 15 mm φ, thickness of 1.5 mm and length of 40 mm were prepared by an injection molding machine, using the pellets obtained.

Embodiments 13 to 15

The resin compositions of embodiments 13 to 15 and the comparative example 8 were obtained in the same manner as the first embodiment except for the (B) component, for which a phosphazene composition, represented by "C" in the type-indicating fields of the TABLES, having the general formula (4) stated below was alternatively used.

Also, the molded articles for the testing each having a cylindrical shape with an inner diameter of 15 mm φ, thickness of 1.5 mm and length of 40 mm were prepared by an injection molding machine, using the pellets obtained.

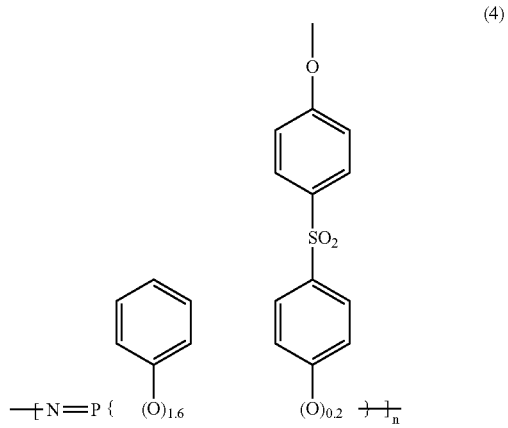

Average molecular weight: 1200

Embodiments 16 to 21

By using a biaxial extruder of 45 mm φ with a resin temperature set at 190° C., the (A) component (for which the same polyamide resin as the first embodiment was used) was poured thereinto and molten. The polyamide resin used is marketed under the name "DAIAMID L-1940". The mixture of the (B) component (for which N-butyl-benzenesulfonamide was used as a sulfone amide derivative) and the (C) component (for which permethrin was used as a pesticide) in the proportions stated in the TABLE 1 was placed into the biaxial extruder through a side hopper thereof with pressure by a plunger pump. Then, the (D) component (for which potassium 8-titanate fiber, represented by "A" in the type-indicating fields of the TABLES herein, having an average fiber diameter of 0.5 μm and average fiber length of 18 μm was used as a fibrous inorganic filler) was fed via a side-feed. The potassium 8-titanate fiber used is marketed under the name of "TISMO-D" and manufactured by OTSUKA KAGAKU KABUSHIKI KAISHA. The resultant was then formed into pellets. Thus, the resin compositions of the embodiments 16 to 21 were obtained.

The molded articles for the testing each having a cylindrical shape with an inner diameter of 15 mm φ, thickness of 1.5 mm and length of 40 mm were prepared by an injection molding machine, using the pellets obtained.

Comparative Example 6

By using a biaxial extruder of 45 mm φ with a resin temperature set at 240° C., 80 weight parts of polypropylene resin, represented by "PP" for convenience in the type-indicating fields of the (A) component was poured thereinto and molten. The polypropylene resin used is marketed under the name of "UBE POLYPRO" and manufactured by UBE INDUSTRIES LTD. 20 weight parts of the (C) component (for which permethrin was used as a pesticide) was placed into the biaxial extruder through a side hopper thereof with pressure by a plunger pump, and then the resultant was formed into pellets. Thus, the resin composition of the comparative example 6 was obtained.

The molded articles for the testing each having a cylindrical shape with an inner diameter of 15 mm φ, thickness of 1.5 mm and length of 40 mm were also prepared for the resin composition of the comparative example 6 by an injection molding machine in the same manner as each embodiment.

Comparative Example 7

By using a biaxial extruder of 45 mm φ with a resin temperature set at 150° C., 80 weight parts of ethylene-vinyl acetate resin, represented by "EVA" for convenience in the type-indicating fields of the (A) component in the TABLES, having a vinyl acetate content of 32% by weight, was poured thereinto and molten. The ethylene-vinyl acetate resin used is marketed under the name of "ULTRASEN 750" and manufactured by TOYO SODA KABUSHIKI KAISHA. 20 weight parts of the (C) component (for which permethrin was used as a pesticide) was placed into the biaxial extruder through a side hopper thereof with pressure by a plunger pump, and then the resultant was formed into pellets. Thus, the resin composition of the comparative example 6 was obtained.

The molded articles for the testing each having a cylindrical shape with an inner diameter of 15 mm φ, thickness of 1.5 mm and length of 40 mm were also prepared for the resin composition of the comparative example 7 by an injection molding machine in the same manner as each embodiment.

Test Example 1

The molded articles for the testing obtained in the respective embodiments and comparative examples were left in an atmosphere of 25° C. After the elapse of 7 days, three months and 6 months respectively, gauzes, which are manufactured by TORAY INDUSTRIES, INC., and marketed under the name of "TETORON C-119 SKYLARK", were attached to the opposite ends of the molded articles and prepared five test objects each keeping one spider (agelena limbata) therein were prepared for each embodiment and comparative example. The life or death of agelena limbata was confirmed in 24 hours.

The life or death of agelena limbata was determined by applying stimuli thereto with a pincette. That is, when no reaction has been observed, it has been determined as being dead.

The test results are shown in the TABLES 1 and 2.

The evaluation of the pesticidal activity shown in the TABLES 1 and 2 was made based upon the proportion of the died test objects with respect to all the test objects (i.e., 5 test objects).

In the TABLES, the symbols, ○, Δ and X respectively represent the death rates of the agelena limbata, namely not less than 80%, between 40 to not more than 80% and not more than 40%.

Test Example 2

Test pieces were prepared by an injection molding technique, using the resin compositions of the embodiments 1 and 4, and the comparative examples 6 and 7, and the tests were conducted to determine the pulling strength (ASTM D638), flexural strength (ASTM D790), heat deflection temperature (ASTM D648, 4.6 kg/cm$^2$) and gasoline resistance.

To evaluate the gasoline resistance, the test pieces each having a cylindrical shape with an inner diameter of 15 mm φ, thickness of 1.5 mm, and length of 40 mm were immersed in gasoline (regular gasoline manufactured by IDEMITSU PETROCHEMICAL CO., LTD.) for 24 hours, and then changes of the test pieces in length were measured just after taking the test pieces out of gasoline.

The test results are shown in TABLE 3.

In the TABLE 3, the symbols ○ and Δ respectively represent the changes of not more than 0.2% and not less than 0.2% in length, and X represents a molten state.

TABLE 3

| | Pulling strength (kgf/cm$^2$) | Flexural strength (kgf/cm$^2$) | Heat deflection temperature (° C.) | Gasoline resistance |
|---|---|---|---|---|
| Embodiment 1 | 370 | 600 | 135 | ○ |
| Embodiment 4 | 550 | 800 | 145 | ○ |
| Comparative Example 6 | 330 | 400 | 108 | Δ |
| Comparative example 7 | <50 | <50 | <40 | X |

As is apparent from the test examples 1 and 2, the molded articles of all the respective embodiments exhibit the pesticidal activity. Particularly, the molded article mixed with the fibrous inorganic filler exhibits an excellent sustained release.

The molded article of each embodiment has a sufficient strength, heat resistance and the like.

As described above, with the pesticidal resin composition of the present invention, it is possible to obtain a pesticidal product that has such a heat resistance and chemical resistance as to enable the resin composition to be used as a structural member or the like, as well as being capable of exhibiting the pesticidal activity for a prolonged period of time.

The invention claimed is:

1. A pesticidal resin composition comprising: (A) at least one resin selected from the group consisting of polyamide resins and polyacetal resins, (B) at least one compound selected from the group consisting of sulfone amides, sulfonic acid esters, carboxylic acid amides and carboxylic acid esters, (C) a chemical agent having a pesticidal property selected from the group consisting of chloronicotinyl insecticides, carbamate compounds, pyrethroid compounds, compounds exhibiting pest growth control activity, and miticides, and (D) fibrous inorganic filler, wherein said fibrous inorganic filler has an average fiber diameter of about 0.05 to about 10 μm and an average fiber length of about 3 to 150 μm, and the proportion of fibrous inorganic filler to at least resin in the composition is from about 2 to about 60 weight parts fibrous inorganic filler to about 100 weight parts resin.

2. A pesticidal resin composition comprising: (A) at least one resin selected from the group consisting of polyamide resins and polyacetal resins, (B) at least one compound selected from the group consisting of sulfone amides, sulfonic acid esters, carboxylic acid amides, and carboxylic acid esters, (C) a chemical agent having a pesticidal property selected from the group consisting of imidacloprid, silafluofen, benfuracarb, alanicarb, metoxadiazone, carbosulfan, phenobcarb, carbaryl, methomyl, propoxur, phenoxycarb, pyrethrin, allethrin, d1-d-T80-allethrin, d-T80-resmethrin, bioallethrin, d-T80-phthalthrin, phthalthrin, resmethrin, furamethrin, proparthrin, permethrin, acrinathrin, etofenprox, tralomethrin, phenothrin, d-phenothrin, fenvalerate, empenthrin, prarethrin, tefluthrin, dichlorovos, fenitrothion, diazinon, malathion, propaphos, fenthion, trichlorform, naled, temephos, fenclophos, chlorpyriphosmethyl, ciafos, calcrofos, azamethiphos, pyridafenthion, propetamphos, chlorpyriphos, methoprene, pyriproxyfen, kinoprene, hydroprene, diofenolan, NC-170, flufenoxuron, diflubenzuron, lufenuron, chlorfluazuron, kelthane, chlorfenapyr, tebufenpyrad, pyridaben, milbemectin and fenpyroximate, and (D) fibrous inorganic filler, wherein said fibrous inorganic filler has an average fiber diameter of about 0.05 to about 10 μm and an average fiber length of about 3 to 150 μm, and the proportion of fibrous inorganic material to at least resin in the composition is from about 2 to about 60 weight parts fibrous inorganic filler to about 100 weight parts resin.

* * * * *